Figure 1:
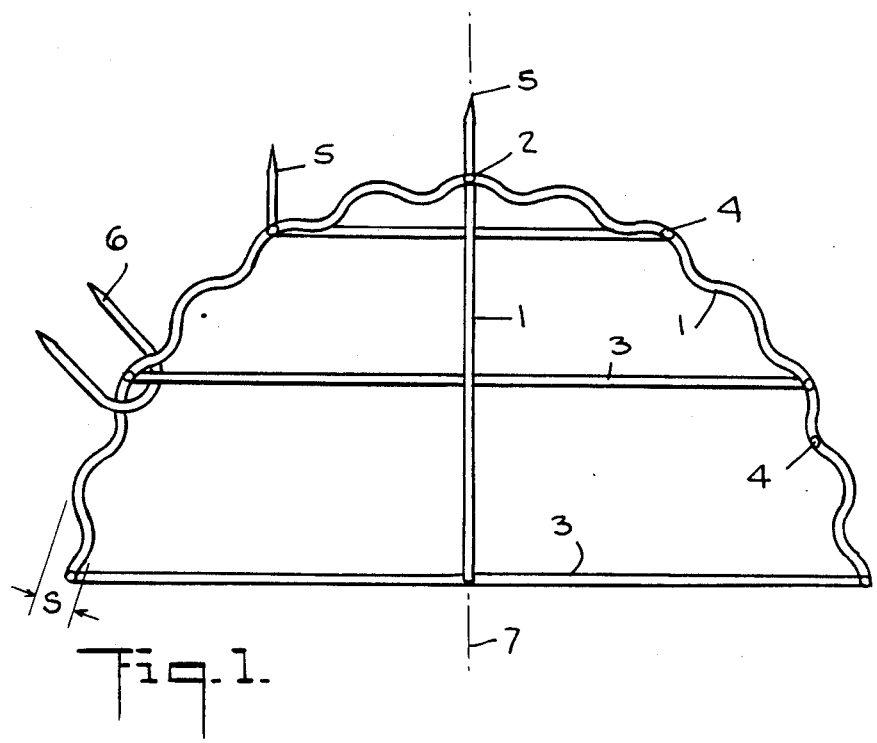

United States Patent [19]

Willert et al.

[11] Patent Number: 4,976,728

[45] Date of Patent: Dec. 11, 1990

[54] REINFORCEMENT FOR A BONE CEMENT BED

[75] Inventors: Hans-Georg Willert, Gottingen, Fed. Rep. of Germany; Maja Burgi, Raterschen, Switzerland

[73] Assignee: Sulzer Brothers Limited, Winterthur, Switzerland

[21] Appl. No.: 330,604

[22] Filed: Mar. 29, 1989

[30] Foreign Application Priority Data

Mar. 29, 1988 [CH] Switzerland .......................... 1182/88

[51] Int. Cl.$^5$ ............................ A61F 2/32; A61F 2/28
[52] U.S. Cl. .......................................... 623/22; 623/16
[58] Field of Search ...................... 623/16, 18, 22, 23; 128/92 YZ, 92 YC

[56] References Cited

U.S. PATENT DOCUMENTS 4,787,899 11/1988 Lazarus ..................................... 623/1
4,813,960 3/1989 Muller ..................................... 623/22
4,856,516 8/1989 Hillstead ................................. 623/1

FOREIGN PATENT DOCUMENTS 2920476 12/1980 Fed. Rep. of Germany ... 128/924 D
2412304 7/1979 France .
8602260 4/1986 World Int. Prop. O. ............ 623/18

OTHER PUBLICATIONS

Vitallium Surgical–Appliances, Catalogue 1964.

*Primary Examiner*—David J. Isabella
*Attorney, Agent, or Firm*—Kenyon & Kenyon

[57] ABSTRACT

The wire mesh reinforcement is provided with a wire mesh lattice having wire-like structures for embedding in a bone cement bed as well as a plurality of spike-like fixing elements which project from the lattice for securement in a bone. The fixing elements serves to anchor the lattice in place before introduction of a bone cement.

13 Claims, 1 Drawing Sheet

U.S. Patent    Dec. 11, 1990    4,976,728

REINFORCEMENT FOR A BONE CEMENT BED

This invention relates to a reinforcement for a bone cement bed and particularly to a wire mesh reinforcement for a bone cement bed.

As is known, various-types of wire mesh reinforcements have been provided about an endoprosthesis for embedment in a bone cement bed. In some cases, the reinforcement has been releasably disposed on the outside surface of the prosthesis and has been formed by at least two sets of corrugations which intersect with each other at least substantially at a right angle.

A reinforcement of the above type, for example, for a fixing stem of a prosthetic femoral head is described in U.S. Pat. No. 4,064,567. When in use, such a reinforcement is drawn over the fixing stem in the manner of a sock and, at implantation, is impacted together with the fixing stem into a bone cement bed which has been previously introduced into the bone. Upon entry, the wires of the reinforcement cut the already polymerizing bone cement into discrete sectors which do not completely "flow together" again to form a closed mass but instead leave at least some "separating walls" between the sectors of cement. As a result, the present trend is to introduce the reinforcement into the bone before introducing the bone cement so that the bone cement, which is still relatively liquid at introduction, flows completely around the reinforcement, thus, the cement is able upon polymerization to form a closed and, apart from the reinforcement, homogeneous cement bed However, difficulties have arisen in pre-cementing fixations, particularly in the case of reinforcements for acetabula which must be anchored in a pelvis since adhesion of the reinforcement in the bone just by resilient clamping has proved unsatisfactory.

Accordingly, it is an object of the invention to provide a reinforcement which can be fixed in an operatively formed cavity in a bone before introduction of a bone cement and of an implant.

It is another object of the invention to provide a wire mesh reinforcement which can be implanted in a bone prior to application of a bone cement bed.

It is another object of the invention to provide a wire mesh reinforcement which can be securely held in a bone cavity prior to implantation of an acetabulum and a bone cement.

Briefly, the invention provides a wire mesh reinforcement for a bone cement bed which is comprised of at least two corrugated wire-like structures disposed in perpendicular crossing relation to each other and a plurality of spike-like fixing elements disposed at least along one of the wire-like structures for securing the structures to a bone.

The spike-like fixing elements are formed so as to be readily pressed into generally spongy bone tissue and ensure adhesion between the reinforcement and the bone until the reinforcement is finally fixed by an entering and curing bone cement.

The wire mesh reinforcement has been shown to be satisfactory as a reinforcement for the cement bed for fixing a hemispherical acetabulum shell. In this case, the wire like structures are disposed on meridian lines of the acetabulum and are connected with a plurality of bearing rings disposed on latitude lines so as to define a hemispherical wide mesh lattice.

Advantageously, one of the fixing elements is disposed at the pole of the hemispherical lattice while other fixing elements, in the form of agraffes, are disposed at intersections between the wire-like corrugated structures and the bearing rings.

In order to ensure a satisfactory uniform thickness of cement bed about the hemispherical wire mesh lattice, the transverse crest spacing of the corrugations is from 2 to 4 millimeters.

The reinforcement may be made of any suitable implant materials with titanium, titanium alloys and stainless steels being the preferred materials.

Figure 2:
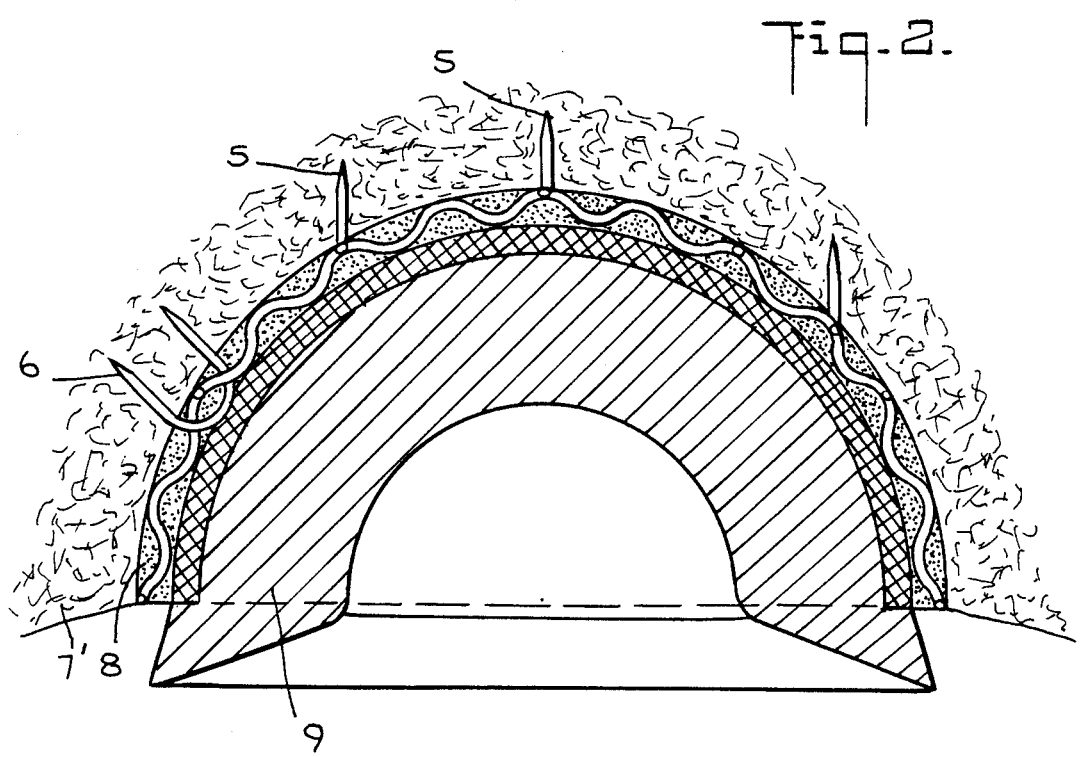

These and other objects and advantages of the invention will become more apparent from the following detailed description taken in conjunction with the accompanying drawings wherein:

FIG. 1 illustrates a diagrammatic view in a meridian section through a reinforcement for an acetabulum in accordance with the invention; and FIG. 2 illustrates a sectional view through a cement-bed-fixed acetabulum with the use of the reinforcement of FIG. 1 in accordance with the invention.

Referring to FIG. 1, the wire mesh reinforcement is formed of a pair of corrugated wire-like structures 1 disposed in perpendicular crossing relation to each other. As indicated, the wire-like structures are curved and disposed on meridian lines, that is, the structures 1 of wire shape extend in meridian planes of an imaginary hemisphere and are interconnected at the pole 2 thereof by soldering or welding.

Each wire-like structure 1 is corrugated with the corrugations having an "amplitude" of a few millimeters i.e. a transverse crest spacing S of from 2 to 4 mm.

The wire mesh reinforcement also has a plurality of bearing rings 3 disposed on latitude lines concentric to an axis of symmetry of 7 of the reinforcement and secured to the wire-like structure 1 to define a hemispherical wide mesh lattice. These rings 3 give stability to the lattice and may be secured to the corrugated structures 1 by soldered or welded joints 4.

The reinforcement also includes a plurality of spike-like fixing elements 5 which are disposed at least along one of the wire-like structures 1 for securing the reinforcement to a bone (not shown). As indicated, the fixing elements 5 extend outwards from the "surface" of the corrugated structures 1 in parallel to the axis of symmetry 7 of the reinforcement and are secured thereto by soldering or welding. The fixing elements 5 are preferably disposed one below another at between-structure intersections or at intersections between the structures 1 and the bearing rings 3. The fixing elements 5 need not be coplanar, as shown, but may have an arbitrary spatial distribution on the surface of the hemispherical-shaped reinforcement.

The fixing elements may also be in the form of agraffes 6 which are either secured to the corrugated structures 1 or rings 3 by way of soldered or welded joints 4 or which extend loosely around the reinforcement from the inside toward the outside.

Referring to FIG. 2, during implantation, the wire mesh reinforcement is initially attached to the spongy tissue 7 of a bone by means of the fixing elements 5, 6. Thereafter, a bone cement bed 8 is applied within the cavity of the bone with the corrugated structures 1 being embedded within the bone cement 8. Thereafter, an acetabulum 9 is pressed into the bone cement.

After the bone cement 8 has hardened, the acetabulum 9 becomes anchored in the bone 7 while a bone cement bed of uniform thickness is formed over the entire surface due to the reinforcement.

The invention thus provides a wire mesh reinforcement which can be embedded in a surgically prepared cavity of a bone prior to formation of bone cement. Further, the invention provides a wire mesh reinforcement which may be securely held in place prior to formation of a bone cement bed and implantation of a prosthesis.

What is claimed is:

1. A wire mesh reinforcement for a bone cement bed comprising
   at least two curved and corrugated structures of wire shape disposed in perpendicular crossing relation to each other to define a hemi-spherical lattice with unobstructed spaces between said structures for receiving bone cement; and
   a plurality of fixing elements of spike shape disposed at least along one of said structures for securing said structures to a bone.

2. A wire mesh reinforcement as set forth in claim 1 wherein each structure has corrugations disposed on a transverse crest spacing of from 2 to 4 millimeters.

3. A wire mesh reinforcement as set forth in claim 1 wherein said structures are disposed on meridian lines.

4. A wire mesh reinforcement as set forth in claim 3 which further comprises a plurality of bearing rings disposed on latitude lines and secured to said structures to define a hemispherical lattice.

5. A wire mesh reinforcement as set forth in claim 4 wherein said fixing elements are disposed at intersections of said rings with said structures.

6. A wire mesh reinforcement as set forth in claim 4 wherein at least one fixing element is disposed at a pole of said lattice.

7. A wire mesh reinforcement for a bone cement bed comprising
   a wire mesh hemi-spherical lattice having a plurality of corrugated structures of wire shape disposed in crossing relation forming latitude lines and a plurality of rings secured on latitude lines for embedding in a bone cement bed; and
   a plurality of fixing elements of spike shape projecting from said lattice for securement in a bone.

8. A wire mesh reinforcement as set forth in claim 7 wherein said fixing elements are fixedly secured to said lattice.

9. A wire mesh reinforcement as set forth in claim 7 wherein said fixing elements extend in parallel to an axis of said lattice.

10. A wire mesh reinforcement for a bone cement bed comprising
    at least two curved and corrugated structures of wire shape disposed in perpendicular crossing relation to each other to define a hemispherical lattice with unobstructed spaces between said structures for bone cement; and
    at least one fixing element of spike shape disposed at a pole of said lattice for securing said lattice to a bone for subsequently receiving bone cement.

11. A wire mesh reinforcement as set forth in claim 10 wherein each structure has corrugations of a height of from 2 to 4 millimeters.

12. A wire mesh reinforcement as set forth in claim 10 which further comprises a plurality of bearing rings disposed on latitude lines and secured to said structures.

13. A wire mesh reinforcement as set forth in claim 12 which further comprises a plurality of fixing elements projecting from said lattice for securement in a bone.

* * * * *